United States Patent [19]

Wiley et al.

[11] 4,238,398

[45] Dec. 9, 1980

[54] ANTIBIOTICS 7(R)-0-ALKYLNOGALAROLS

[75] Inventors: Paul F. Wiley, Kalamazoo; David J. Houser, Portage, both of Mich.

[73] Assignee: The Upjohn Company, Kalamazoo, Mich.

[21] Appl. No.: 89,967

[22] Filed: Oct. 31, 1979

Related U.S. Application Data

[63] Continuation-in-part of Ser. No. 970,341, Dec. 18, 1978, abandoned.

[51] Int. Cl.³ .................................... C07D 319/08
[52] U.S. Cl. ............................ 260/340.3; 424/278
[58] Field of Search ...................... 260/340.3

[56] References Cited

U.S. PATENT DOCUMENTS

| | | | |
|---|---|---|---|
| 3,183,157 | 5/1965 | Bhuyan et al. | 424/181 |
| 3,501,569 | 3/1970 | Wiley et al. | 424/278 |
| 4,086,245 | 4/1979 | Wiley et al. | 260/340.3 |

*Primary Examiner*—Ethel G. Love
*Attorney, Agent, or Firm*—Roman Saliwanchik

[57] ABSTRACT

Novel antibiotics, 7(R)-0-alkylnogalarols, prepared by acidic alcoholysis of nogalamycin of nogalarol, which are active against various microorganisms, for example, *Bacillus subtilis, Streptococcus pyogenes, Sarcina lutea, Bacteroides fragilis, Clostridium perfringens,* and *Mycobacterium avium.* Thus, they can be used to inhibit the growth of the above microorganisms in various environments. Further, the invention compounds possess unexpected superior activity against P388 leukemia infection in laboratory mice. Thus, the compounds of the invention can be used to treat laboratory mice infected with P388 leukemia.

7 Claims, No Drawings

ANTIBIOTICS 7(R)-O-ALKYLNOGALAROLS

The invention described herein was made in the course of, or under Contract N01-CM-77100 with the National Cancer Institute, National Institutes of Health, Bethesda, Maryland 20014.

CROSS REFERENCE TO RELATED APPLICATION

This is a continuation-in-part of our pending application Ser. No. 970,341, filed Dec. 18, 1978, now abandoned.

BACKGROUND OF THE INVENTION

The known antibiotic nagalamycin, and a process for its preparation, are described in U.S. Pat. No. 3,183,157. The structure of nogalamycin can be shown as follows:

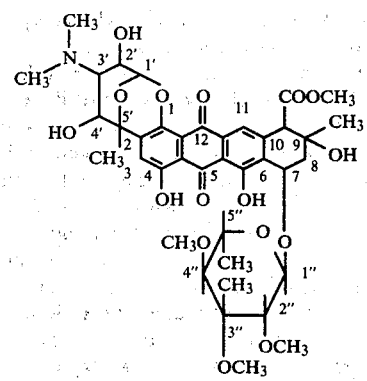

Antibiotics nogalarol and nogalarene, produced by acid hydrolysis of nogalamycin, and o-methylnogalarol, produced by acidic methanolysis of nogalamycin or nogalarol, are disclosed in U.S. Pat. No. 3,501,569.

U.S. Pat. No. 3,501,569 concerns, inter alia, 7-O-methylnogalarol and its preparation from nogalamycin or nogalarol. It is now known that this compound is the (S) form and, that, also produced in the process, but heretofore not recognized or recovered, are the compounds of the subject invention which are the (R) form. The compound of U.S. Pat. No. 3,501,569 can be shown as follows:

7(S)-O-Methylnogalarol

BRIEF SUMMARY OF THE INVENTION

7(R)-O-Alkylnogalarols can be prepared by acidic alcoholysis of nogalamycin or nogalarol. For example, upon reacting nogalamycin or nogalarol with methanolic hydrogen chloride at a temperature of about 50° C. to reflux, there is obtained 7(S)-O-methylnogalarol (U-23,482) and 7(R)-O-methylnogalarol (U-55,370). These compounds can be recovered from the reaction mixture by chromatographic means which effectively separate them into distinct entities. By substituting ethanolic, propanolic, and butanolic hydrogen chloride in the above reaction, there are obtained the corresponding 7(S)-O- and 7(R)-O-alkylnogalarols.

The 7(R)-O-alkylnogalarols of the subject invention are biologically active and can be used in various environments to inhibit the growth of susceptible microorganisms. For example, these compounds can be used for treating breeding places of silkworms, to prevent or minimize infections which are well known to be caused by *Bacillus subtilis*. Further, these compounds can be used to minimize or prevent odor in fish and fish crates caused by contamination with *B. subtilis*. Also, 7(R)-O-ethylnogalarol and 7(R)-O-methylnogalarol can be used to treat birds infected with *Mycobacterium avium*. The antimicrobial spectra of 7(R)-O-methylnogalarol, 7(R)-O-ethylnogalarol, and 7(R)-O-propylnogalarol is as follows:

| | Zone Size (mm) | | |
|---|---|---|---|
| Microorganism | 7(R)-O-Propyl-nogalarol | 7(R)-O-Ethyl-nogalarol | 7(R)-O-Methyl-nogalarol |
| *Bacillus subtilis* (syn.)* | Tr | 29 | 15 |
| *Bacillus subtilis* (nutr.) | 15 | 29 | 20 |
| *Staphylococcus aureus* | 0 | 19 | 0 |
| *Streptococcus pyogenes* | 17 | 30 | 23 |
| *Mycobacterium avium* | 0 | 23 | 17 |
| *Proteus vulgaris* | 0 | 0 | 0 |
| *Salmonella schottmuelleri* | 0 | 0 | 0 |
| *Salmonella gallinarum* | 0 | 0 | 0 |
| *Escherichia coli* (syn.) | 0 | 0 | 0 |
| *Escherichia coli* (nutr.) | 0 | 0 | 0 |
| *Klebsiella pneumoniae* | 0 | 0 | 0 |
| *Sarcina lutea* UC130 | Tr | 25 | Tr |
| *Sarcina lutea* 3383 | 0 | 21 | 20 |
| *Staphylococcus aureus* 6029 | 0 | 19 | 0 |
| *Staphylococcus aureus* 3665 | 0 | Tr | 0 |
| *Bacteroides fragilis* | 25 | 35 | 31 |
| *Clostridium perfringens* | 20 | 23 | 23 |
| *Rhodopseudomonas spheroides* | 0 | Tr | Tr |
| *Pseudomonas aeruginosa* | 0 | 0 | 0 |
| *Saccharomyces pastorianus* | 0 | 0 | 0 |
| *Penicillium oxalicum* | 0 | 0 | 0 |

*Bacillus subtilis* (synthetic medium) has the following composition:

| | |
|---|---|
| $Na_2HPO_4 \cdot 7H_2O$ | 1.7 g |
| $KH_2PO_4$ | 2.0 g |
| $(NH_4)_2SO_4$ | 1.0 g |
| $MgSO_4$ | 0.1 g |
| Glucose | 2.0 g |
| Bacto Agar[1] | 15.0 g |
| Distilled Water | 1 liter |
| Metallic Ion Stock Solution[2] | 1 ml |

[1] Bacto Agar obtained from Difco Laboratories, Detroit, Michigan.
[2] Metallic Ion Stock Solution consists of the following:

| | |
|---|---|
| $NaMoO_4 \cdot 2H_2O$ | 200 µg/ml |
| $CoCl_2$ | 100 µg/ml |
| $CuSO_4$ | 100 µg/ml |
| $MnSO_4$ | 2 mg/ml |
| $CaCl_2$ | 25 mg/ml |
| $FeCl_2 \cdot 4H_2O$ | 5 mg/ml |
| $ZnCl_2$** | 5 mg/ml |

**$ZnCl_2$ has to be dissolved separately using a drop of 0.1 N HCl for 10 ml of water. The stock solution is heated to bring all the compounds in solution, kept standing for 24 hours, and sterile filtered.

The above antimicrobial tests were run by dipping 6.5 mm filter paper discs into a 1 mg/ml solution of the test substance in methanol and placing the discs on agar plates containing a 1.3 mm layer of agar freshly seeded with the test organism. Discs dipped in methanol alone gave no inhibition zones. The plates were incubated 18 to 24 hours at 37° C. before reading the zones.

DETAILED DESCRIPTION OF THE INVENTION

The 7(R)-O-alkylnogalarols of the subject invention can be shown by the following structure:

7(R)-O-Alkylnogalarois.

wherein R is an alkyl group of from 1 to 4 carbon atoms, inclusive.

7(R)-O-Alkylnogalarols can be prepared by acidic alcoholysis of nogalamycin or nogalarol. The reaction can be conducted with a mineral acid ranging from about 0.05 N to about 1 N. Examples of acids which can be used are hydrogen chloride, hydrogen bromide, hydrogen iodide, sulfuric acid, phosphoric acid, and the like.

The reaction can be conducted at a temperature of about 50° C. to reflux. Reflux is preferred as lower temperatures prolong the completion of the reaction.

Suitable alcohols which can be used in the reaction are methanol, ethanol, propanol, isopropanol, n-butanol, and isobutanol.

The products can be recovered from the extract by chromatography on silica gel using the solvent system $CHCl_3$—$CH_3OH$ (95:5).

7(R)-O-Alkylnogalarol can be acylated under standard acylating conditions with an appropriate acid halide or anhydride to give the acylated compound. The acylation is carried out in the presence of an acid-binding agent. Suitable acid-binding agents include: amines such as pyridine, quinoline, and isoquinoline, and buffer salts such as sodium acetate. The preferred base is pyridine. Carboxylic acids suitable for acylation include (a) saturated or unsaturated, straight or branched chain aliphatic carboxylic acids, for example, acetic, propionic, butyric, isobutyric, tertbutylacetic, valeric, isovaleric, caproic, caprylic, decanoic, dodecanoic, lauric, tridecanoic, myristic, pentadecanoic, palmitic, margaric, stearic, acrylic, crotonic, undecylenic, oleic, hexynoic, heptynoic, octynoic acids, and the like; (b) saturated or unsaturated, alicyclic carboxylic acids, for example, cyclobutanecarboxylic acid, cyclopentanecarboxylic acid, cyclopentenecarboxylic acid, methylcyclopentenecarboxylic acid, cyclohexanecarboxylic acid, dimethylcyclohexanecarboxylic acid, dipropylcyclohexanecarboxylic acid, and the like; (c) saturated or unsaturated, alicyclic aliphatic carboxylic acids, for example, cyclopentaneacetic acid, cyclopentanepropionic acid, cyclohexaneacetic acid, cyclohexanebutyric acid, methylcyclohexaneacetic acid, and the like; (d) aromatic carboxylic acids, for example, benzoic acid, toluic acid, naphthoic acid, ethylbenzoic acid, isobutylbenzoic acid, methylbutylbenzoic acid, and the like; and (e) aromatic aliphatic carboxylic acids, for example, phenylacetic acid, phenylpropionic acid, phenylvaleric acid, cinnamic acid, phenylpropiolic acid, and naphthylacetic acid, and the like. Also, suitable halo-, nitro-, amino-, cyano-, and lower alkoxy-hydrocarbon carboxylic acids include hydrocarboncarboxylic acids as given above which are substituted by one or more of halogen, nitro, amino, cyano, or lower alkoxy, advantageously lower alkoxy of not more than six carbon atoms, for example, methoxy, ethoxy, propoxy, butoxy, amyloxy, hexyloxy groups and isomeric forms thereof. Examples of such substituted hydrocarbon carboxylic acids are:

mono-, di- and trichloroacetic acid;
α- and β- chloropropionic acid;
α- and γ-bromobutyric acid;
α- and δ-iodovaleric acid;
mevalonic acid;
2- and 4-chlorocyclohexanecarboxylic acid;
shikimic acid;
2-nitro-1-methyl-cyclobutanecarboxylic acid;
1,2,3,4,5,6-hexachlorocyclohexanecarboxylic acid;
3-bromo-2-methylcyclohexanecarboxylic acid;
4- and 5-bromo-2-methylcyclohexanecarboxylic acid;
5- and 6-bromo-2-methylcyclohexanecarboxylic acid;
2,3-dibromo-2-methylcyclohexanecarboxylic acid;
2,5-dibromo-2-methylcyclohexanecarboxylic acid;
4,5-dibromo-2-methylcyclohexanecarboxylic acid;
5,6-dibromo-2-methylcyclohexanecarboxylic acid;
3-bromo-3-methylcyclohexanecarboxylic acid;
6-bromo-3-methylcyclohexanecarboxylic acid;
1,6-dibromo-3-methylcyclohexanecarboxylic acid;
2-bromo-4-methylcyclohexanecarboxylic acid;
1,2-dibromo-4-methylcyclohexanecarboxylic acid;
3-bromo-2,2,3-trimethylcyclopentanecarboxylic acid;
1-bromo-3,5-dimethylcyclohexanecarboxylic acid;
homogentisic acid, o-, m-, and p-chlorobenzoic acid;
anisic acid;
veratric acid;
trimethoxybenzoic acid;
trimethoxycinnamic acid;
4,4'-dichlorobenzilic acid;
o-, m-, and p-nitrobenzoic acid;
cyanoacetic acid;
3,4- and 3,5-dinitrobenzoic acid;
2,4,6-trinitrobenzoic acid;
cyanopropionic acid;
ethoxyformic acid (ethyl hydrogen carbonate);
and the like.

The acylated compounds, as described above, can be used in animals for the same biological purposes as disclosed above for 7(R)-O-alkylnogalarols. For example, the acylated compounds can be given in oral form to an animal possessing the necessary enzyme to remove the acyl group, thus freeing the parent antibiotic compound which then inhibits susceptible bacteria.

Acid addition salts of 7(R)-O-alkylnogalarols can be made by neutralizing the compound with an appropriate acid to below about pH 7.0, and advantageously to about pH 2 to pH 6. Suitable acids for this purpose include tartaric, glucuronic, and lactic which give water soluble salts, and hydrochloric, sulfuric, phosphoric, sulfamic, hydrobromic, and the like which give relatively water insoluble salts. Acid salts of 7(R)-O-alkylnogalarols can be used for the same biological purposes as the parent compound.

The following examples are illustrative of the process and products of the invention, but are not to be construed as limiting. All percentages are by weight and all solvent mixture proportions are by volume unless otherwise noted.

EXAMPLE 1—7(R)-O-Methylnogalarol

A solution of 10 g of nogalamycin, obtained as disclosed in U.S. Pat. No. 3,183,157, in 500 ml of dry 0.5 N methanolic HCl is heated under reflux for 5 hours. The volume is reduced to 150 ml by evaporation under reduced pressure. The resulting solvent is diluted with 250 ml of water and extracted with two 100-ml portions of $CHCl_3$. The remaining aqueous solution is adjusted to pH 7 with 50% sodium hydroxide solution and extracted with several portions of $CHCl_3$. Evaporation of the combined $CHCl_3$ extracts under reduced pressure gives 8.03 g of dark red residue.

Five grams of the crude material is chromatographed on a 250 g silica gel column by HPLC (High Performance Liquid Chromatography) using the solvent system $CHCl_3$—$CH_3OH$ (95:5). A total of three hundred and five 5-ml fractions are collected. 7(S)-O-Methylnogalarol is found in fractions 261–280. Fractions 171–200 are combined on the basis of tlc (thin layer chromatography) ($CHCl_3$-$CH_3OH$-$H_2O$; 78:20:2; Rf 0.64) and evaporated to dryness under reduced pressure, yield 0.31 g of essentially pure 7(R)-O-methylnogalarol. A further 0.59 g of the same material, but slightly less pure as judged by tlc, is obtained from fractions 151–170; mp 200° dec.; $[\alpha]_D$ 627° (C 0.516, $CHCl_3$); uv (EtOH) $\lambda$max nm 236 ($\epsilon$ 43,400), 252 ($\epsilon$ 25,750), 257sh ($\epsilon$ 24,350), 290sh ($\epsilon$ 11,400), 480 ($\epsilon$ 15,600); ir (Nujol) 3440, 3180, 1740, 1665, 1615, 1575, 1300, 1285, 1260, 1230, 1125, 1105, and 1005 $cm^{-1}$; $^1$H NMR ($CHCl_3$) $\delta$ 1.59 (s, 3 H, $CH_3C$), 1.71 (s, 3 H, $CH_3C$), 2.03 (m, 1 H, H-8a), 2.25 (m, 1 H, H-8b), 2.56 [s, 6 H, $(CH_3)_2N$], 3.53 (s, 3 H, $CH_3O$), 3.70 (s, 3 H, $CH_3O$), 3.6–4.0 (m, 5 H, C<u>H</u>O and C<u>H</u>N), 4.87 (m, 1 H, H-7), 5.87 (d, 1 H, H-1'), 6.51 (s, 1 H, H-3), 7.24 (s, 1 H, H-11); $^{13}$C NMR ($CDCl_3$) $\delta$ 23.9 (C-5' $CH_3$), 28.9 (C-9 $CH_3$), 37.6 (C-8), 41.5 [$(CH_3)_2N$], 52.0 ($COOCH_3$), 57.5 (C-10), 58.0 (C-7 $CH_3O$), 65.9 (C-3'), 69.5 (C-7), 70.1 (C-9), 70.5 (C-4'), 72.9 (C-2'), 75.2 (C-5'), 97.8 (C-1'), 112.9 (C-5a), 114.2 (C-4a), 115.8 (C-12a), 121.2 (C-11), 125.8 (C-3), 129.8 (C-6a), 132.8 (C-11a), 138.2 (C-2), 143.6 (C-10a), 148.6 (C-1), 155.8 (C-4), 160.8 (C-6), 171.1 ($COOCH_3$), 179.0 (C-12), 190.8 (C-5); mass spectrum, M+ 599. Anal. calcd. for $C_{30}H_{33}NO_{12}$: C, 60.16; H, 5.51; N, 2.34. Found: C, 58.57; H, 5.53; N, 2.32.

EXAMPLE 2—7(R)-O-ETHYLNOGALAROL

Ten grams of nogalamycin is dissolved in 500 ml of absolute ethanol 0.14 N in HCl. The solution is heated under reflux for 5½ hours followed by overnight stirring at room temperature. The solution is concentrated to about 250 ml by evaporation under reduced pressure. It is then diluted with 50 ml of water and extracted with two 150-ml portions of $CHCl_3$. The aqueous residue is adjusted to pH 7 with 50% NaOH solution. The neutral solution is extracted with one 200-ml portion and two 100-ml portions of $CHCl_3$. Evaporation under reduced pressure gives a residue which was chromatographed on 450 g of silica gel using $CHCl_3$-$CH_3OH$ (95:5) and collecting four hundred and twenty 10-ml fractions. The fractions are pooled on the basis of tlc analysis using $CHCl_3$-$CH_3OH$-$H_2O$ (78:20:2) into pool 1 (fractions 65–110) with Rf 0.74 and pool 2 (fractions 160–220) with Rf 0.64 although the second pool contained a little of the more mobile material. 7(S)-O-Ethylnogalarol is found in fractions 160–220. Evaporation of pool 1 under reduced pressure gives 1.56 g of essentially pure 7(R)-O-ethylnogalarol.

Three hundred mg of 7(R)-O-ethylnogalarol is chromatographed on 20 g of silica gel using HPLC and the solvent system $CHCl_3$-$CH_3OH$ (98:2). Sixty-five 5-ml fractions are collected. Analysis by tlc as above results in combining fractions 31–50 into a pool which was evaporated under reduced pressure to give 13 mg of material which was homogeneous by tlc in $CHCl_3$-$CH_3OH$-$H_2O$ (78:20:2). Analysis and an infrared spectrum were obtained from this material, and other characterization data were obtained from material from the first chromatography; mp 255°–260° dec.; $[\alpha]_D$ 698° (C 0.0975, $CHCl_3$); uv (EtOH) $\lambda$max nm 236 ($\epsilon$ 45,800), 258 ($\epsilon$ 22,050) 288sh ($\epsilon$ 10,750), 480 ($\epsilon$ 14,900); ir (Nujol) 3460, 3180, 1740, 1665, 1620, 1575, 1300, 1275, 1255, 1220, 1105, 1055, and 1005 $cm^{-1}$; $^1$H NMR ($CDCl_3$) $\delta$ 1.23 (s, 3 H, $CH_3CH_2$), 1.55 (s, 3 H, $CH_3C$), 1.76 (s, 3 H, $CH_3C$), 2.61 [s, 6 H, $(CH_3)_2N$], 2.1–2.5 (m, 2 H), 3.73 (s, 3 H, $CH_3O$), 3.0–4.5 (m, 7 H, CHO and CHN), 4.91 (s, 1 H, OH), 5.06 (m, 1 H, H-7), 5.92 (d, 1 H, H-1'), 6.52 (s, 1 H, H-3), 7.23 (s, 1 H, H-11); $^{13}$C NMR ($CDCl_3$) $\delta$ 15.4 ($CH_3CH_2$), 23.9 (C-5' $CH_3$), 29.8 (C-9 $CH_3$), 38.0 (C-8), 41.5 [$(CH_3)_2N$], 52.0 ($COOCH_3$), 57.5 (C-10), 66.0 (C-3') 66.0 ($CH_3\underline{C}H_2O$), 68.4 (C-7), 69.5 (C-9), 70.5 (C-4'), 72.8 (C-2'), 75.2 (C-5'), 97.9 (C-1'), 112.8 (C-5a), 114.2 (C-4a), 115.8 (C-12a), 121.3 (C-11), 125.7 (C-3), 130.2 (C-6a), 132.7 (C-11a), 138.1 (C-2), 143.5 (C-10a), 148.5 (C-1), 155.7 (C-4), 160.7 (C-6), 171.0 ($COOC_2H_5$), 178.9 (C-12), 190.8 (C-5); mass spectrum, M+ 613. Anal. calcd. for $C_{31}H_{35}NO_{12}$: C, 60.69; H, 5.71; N, 2.28. Found: C, 59.42; H, 5.76; N, 2.17.

EXAMPLE 3—7(R)-O-n-PROPYLNOGALAROL

Ten grams of nogalamycin is dissolved in 500 ml of n-propanol 0.14 N in HCl, and the solution is heated under reflux for 2½ hours followed by evaporation under reduced pressure to a volume of 200 ml and dilution with 500 ml of $H_2O$. The aqueous solution is extracted with two 150-ml portions of $CHCl_3$. These are combined and evaporated under reduced pressure to a thick residue which was diluted with Skellysolve B. The precipitate formed is removed by filtration and dissolved in 50 ml of water. The solution is adjusted to pH 7 with NaOH and extracted wih three 25-ml portions of $CHCl_3$. Evaporation of the combined extracts under reduced pressure gives 1.5 g of residue which was a mixture of the two isomers as judged by tlc in $CHCl_3$-$CH_3OH$-$H_2O$ (78:20:2). The aqueous residue remaining after the first $CHCl_3$ extraction is neutralized (pH 7) with NaOH and extracted with three 150-ml portions of $CHCl_3$. The combined extracts are evaporated to dryness under reduced pressure. The residue is dissolved in 150 ml of acetone, and 350 ml of Skellysolve B is added. The yield of solid after filtration is 5.6 g. This material is very similar to the 1.5 g previously obtained.

The first residue isolated (1.5 g) is chromatographed by HPLC on a 60 g silica gel column using $CHCl_3$-$CH_3OH$ (95:5) for elution. Ten-ml fractions are collected until two colored materials have been eluted. 7(S)-O-n-Propylnogalarol is found in fractions 71–90. Fractions 18–40 are combined as the first colored maximum and evaporated under reduced pressure to give a solid. The residue is dissolved in 5 ml of acetone and added to 75 ml of Skellysolve B. The resulting precipitate is removed by filtration. The yield of essentially pure 7(R)-O-n-propylnogalarol is 0.48 g, homogeneous by tlc in the above system (Rf 0.73); mp 190°–211° dec.;

[α]$_D$ 586° (C 0.191, CHCl$_3$); uv (EtOH) λmax nm 236 (ε 48,450), 258 (ε 22,800), 287 (ε 10,250), 481 (ε 15,150); ir (Nujol) 3460, 3180, 1745, 1665, 1620, 1575, 1300, 1280, 1255, 1225, 1105, 1055, and 1010 cm$^{-1}$; $^1$H NMR (CDCl$_3$) δ 0.90 (ε, 3 H, CH$_3$CH$_2$), 1.64 (s, 3 H, CH$_3$C), 1.70 (s, 3 H, CH$_3$C), 1.95-2.5 (m, 4 H, CH$_2$), 2.62 [s, 6 H, (CH$_3$)$_2$N], 3.75 (s, 3 H, CH), 2.9-4.5 (m, CHO and CHN), 4.86 (s, 1 H, OH), 5.02 (m, 1 H, H-7), 5.89 (d, 1 H, H-1'), 6.48 (s, 1 H, H-3), 7.18 (s, 1 H, H-11); $^{13}$C NMR (CDCl$_3$) δ 10.5 (CH$_3$CH), 23.1 (CH$_3$CH$_2$CH$_2$), 23.9 (C-5' CH$_3$), 29.7 (C-9 CH$_3$), 37.9 (C-8), 41.5 [(CH$_3$)$_2$N], 51.9 (COOCH$_3$), 57.5 (C-10), 65.8 (C-3'), 68.6 (C-7), 69.5 (C-9), 70.4 (C-4'), 72.3 (CH$_3$CH$_2$CH$_2$O), 72.7 (C-2'), 75.1 (C-5'), 97.7 (C-1'), 112.8 (C-5a), 114.1 (C-4a), 115.7 (C-12a), 121.2 (C-11), 125.7 (C-3), 130.2 (C-6a), 132.6 (C-11a), 138.2 (C-2), 143.6 (C-10a), 148.5 (C-1), 155.5 (C-4), 160.7 (C-6), 171.0 (COOCH$_3$), 178.9 (C-12), 190.7 (C-5); mass spectrum m/e (FD) 627. Anal. calcd. for C$_{32}$H$_{37}$NO$_{12}$: C, 61.30; H, 5.95; N, 2.23. Found: C, 60.83; H, 6.16; N, 2.04.

EXAMPLE 4

By substituting N-butanol or isobutanol for methanol in Example 1, there is obtained the corresponding essentially pure 7(R)-O-butylnogalarol.

EXAMPLE 5

By substituting nogalarol for nogalamycin in Example 1, there is obtained essentially pure 7(R)-O-methylnogalarol.

EXAMPLE 6

By substituting nogalarol for nogalamycin in Example 2, there is obtained essentially pure 7(R)-O-ethylnogalarol.

EXAMPLE 7

By substituting nogalarol for nogalamycin in Example 3, there is obtained essentially pure 7(R)-O-n-propylnogalarol.

EXAMPLE 8

By substituting nogalarol for nogalamycin in Example 4, there is obtained essentially pure 7(R)-O-butylnogalarol.

The antitumor cell activity of the compounds of the invention was compared with the 7(S)-O-alkylnogarols. The tests were run according to the protocols of the Division of Cancer Treatment, National Cancer Institute. Saline suspensions of tumor cells from murine P388 leukemia and murine B16 melanoma were injected into laboratory mice. The mice were then dosed with the test drugs and the following results were obtained.

|  | P388 Leukemia | | B16 Melanoma | |
|---|---|---|---|---|
|  | Dose (mg/kg/day) | % ILS* | Dose (mg/kg/day) | % ILS |
| 7(S)-O-methyl-nogalarol | 25 | 60 | 50 | 84 |
| 7(R)-O-methyl-nogalarol | 25 | 98 | 10 | 35 |

*% ILS = % increased life span of infected mice given the drug over infected mice which were not given the drug.

The results show clearly that the 7(R)-O-methylnogalarol of the subject invention is unexpectedly superior to 7(S)-O-methylnogalarol in treating laboratory mice infected with P388 leukemia tumor cells.

We claim:

1. Essentially pure 7(R)-O-alkylnogalarols, compounds having the following structure:

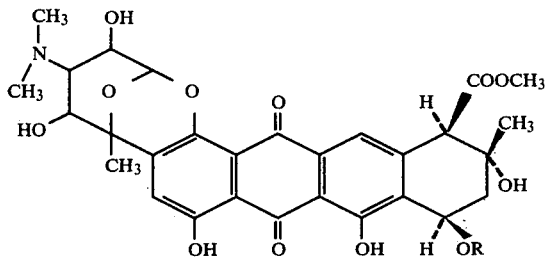

wherein R is alkyl of from 1 to 4 carbon atoms, inclusive.

2. Biologically acceptable acid addition salts of the compound of claim 1.

3. 7(R)-O-Methylnogalarol, a compound according to claim 1, wherein R is methyl.

4. 7(R)-O-Ethylnogalarol, a compound according to claim 1, wherein R is ethyl.

5. 7(R)-O-Propylnogalarol, a compound according to claim 1, wherein R is propyl.

6. 7(R)-O-Butylnogalarol, a compound according to claim 1, wherein R is butyl.

7. Acylates of 7(R)-O-alkylnogalarol wherein said acyl group consists of hydrocarbon carboxylic acid acyl of from 2 to 18 carbon atoms, inclusive; halo-, nitro-, amino-, cyano-, and lower alkoxy-substituted hydrocarbon, carboxylic acid acyl of from 2 to 18 carbon atoms, inclusive.

* * * * *